United States Patent [19]

Dawson

[11] Patent Number: 4,943,525
[45] Date of Patent: Jul. 24, 1990

[54] SIMULTANEOUS IMMUNOASSAY FOR THE DETERMINATION OF ANTIGENS AND ANTIBODIES

[75] Inventor: Elliott Dawson, Bellbuckle, Tenn.

[73] Assignee: BioVentures, Inc., Murfreesboro, Tenn.

[21] Appl. No.: 115,955

[22] Filed: Nov. 2, 1987

[51] Int. Cl.[5] .................. G01N 33/53; G01N 33/536; G01N 33/542; C12Q 1/34

[52] U.S. Cl. .......................................... 435/7; 435/14; 435/15; 435/18; 435/28; 436/500; 436/512; 436/536; 436/537; 436/548; 436/813

[58] Field of Search .................... 435/7, 14, 15, 18, 28; 436/500, 512, 536, 537, 548, 813, 540

[56] References Cited

U.S. PATENT DOCUMENTS

| | | | |
|---|---|---|---|
| 4,366,241 | 12/1982 | Tom et al. | 435/7 |
| 4,595,655 | 6/1986 | Self | 435/7 |
| 4,598,042 | 7/1986 | Self | 435/7 |
| 4,629,688 | 12/1986 | Boguslaski et al. | 436/537 X |
| 4,633,278 | 5/1987 | DiNello | 435/7 |
| 4,654,300 | 3/1987 | Suk et al. | 435/7 |
| 4,661,445 | 4/1987 | Saxinger et al. | 435/7 |
| 4,672,044 | 6/1987 | Schreiber | 435/7 |
| 4,687,735 | 8/1987 | DiNello et al. | 435/7 |
| 4,695,538 | 9/1987 | Cole et al. | 435/7 |
| 4,769,321 | 9/1988 | Self | 435/7 |
| 4,791,055 | 12/1988 | Boguslaski et al. | 435/7 |

OTHER PUBLICATIONS

Ngo and Lenhoff, "Biochemical and Biophysical Research Comm.", vol. 99, No. 2,. pp. 496-503 (1981).
Kurstak, E., "Bulletin of the World Health Organization", 63(4): pp. 7930811 (1985).
Van Weemen, B., "J. of Virological Methods", 10, pp. 371, 378 (1985).
Barre-Sinoussi, F. et al., "Isolation of a T-Lymphotropic Retrovirus from a Patient at Risk for Acquired Immune Deficiency Syndrome (AIDS)." Science, vol. 220, May 20, 1983, pp. 868-871.
Bayer, Edward A. and Wilchek, Meir. Methods of Biochemical Analysis. "The Use of Avidin-Biotin Complex as a Tool in Molecular Biology", vol. 26, 1980, pp. 1-45.
Bergmeyer, Hans, Ulrich, Ed. Methods of Enzymatic Analysis, "Enzymes L: Oxidoreductanses, Transferases", 3rd ed., vol. III, 1983, pp. 553-559.
Bergmeyer, Hans Ulrich , Ed. Methods of Enzymatic Analysis, "Fundamentals", 3rd ed., vol. I, 1983, pp. 348-368.
Cox, C. et al., "An Enzymatic Cycling Procedure for NAD+ Using an Irreversible Reaction with NAD-+-Peroxidase", Analytical Biochemistry, vol. 119, 1982, pp. 185-193.
Cumber, A. J. et al. Methods in Enzymology, "Preparation of Antibody—Toxin Conjugates", vol. 112, (Academic Press Inc., 1985), pp. 207-225.
Domingo, Derrick L. and Trowbridge, Ian S., Methods in Enzymology, "Transferrin Receptor as a Target for Antibody-Drug Conjugates", vol. 112, (Academic Press Inc., 1985), pp. 238-247.
Gallo, Robert C. et al., "Frequent Detection and Isolation of Cytophathic Retroviruses (HTLV-III) from Patients with AIDS and at Risk for AIDS", Science, vol. 224, May 4, 1984, pp. 500-503.
Harper, J. R., and Orengo, A., "The Preparation of an Immunoglobulin-Amyloglucosidase Conjugate and its Quantitation by an Enzyme-Cycling Assay", Analytical Biochemistry, vol. 113, 1981, pp. 51-57.
Kemp, Bruce E. et al., AAAS, "Autologous Red Cell Agglutination Assay for HIV-1 Antibodies: Simplified Test with Whole Blood", Science, vol. 241, Sep. 9, 1988, pp. 1352-1354.
Masseyeff, Rene P and Malvano, Renzo., Methods of Enzymatic Analysis. "Problems in Standardization of Enzyme-Immunoassays for Antigens", 3rd ed., vol. IX, 1983, pp. 38-53.
Martinek, Karel and Mozhaev, V. V., Advances in Enzymology and Related Areas of Molecular Biology, "Simulation of Microenvironmental and Diffusional Effects in Membrane Systems". A. Meister, ed. (New York: Cornell Univ. Medical College), vol. 57, 1985, pp. 218-247.
Mollering, Hans et al., Methods of Enzymatic Analysis, "Visualization of NAD(P)-Dependent Reactions", 3rd ed. vol. IX, Proteins and Peptides, pp. 136-144.
O'Brien, R. D., The Receptors: A Comprehensive Treatise. "Problems and Approaches in Noncatalytic Biochemistry", Cornell Univ., Ithaca, N.Y., Ch. 8, pp. 311-335.
Oellerich, Michael, Methods of Enzymatic Analysis. "Principles of Enzymeimmunoassays." 3rd ed., vol. I, ch. 2.7, 1983, pp. 233-260.
O'Malley, Bert W. Ed. Methods in Enzymology, "Harmone Action, Part B, Peptide Hormones", vol. XXXVII, 1975, pp. 134, 135.
O'Shannessy, Daniel J. et al., "A Novel Procedure for Labeling Immunoglobulins by Conjugation to Oligosac-Charide Moieties", Immunology Letters, vol. 8, 1984, pp. 273-277.
Passonneau, Janet V, and Lowrey, Oliver H., Methods of Enzymatic Analysis, "Kinetics of Enzymatic Cy- (List continued on next page.)

Primary Examiner—Jack Spiegel
Attorney, Agent, or Firm—Sigalos, Levine & Montgomery

[57] ABSTRACT

An immunochemical assay to determine the presence or concentration of antigen or antibodies in a fluid, comprising: (a) forming a ternary complex of a first labelled antibody or antigen, a second labelled antibody or antigen, and the antigen or antibody to be determined; and (b) detecting a signal produced in the presence of at least one substrate, by an interaction between said first label and said second label, enhanced by their proximity to each other bound to the antigenic substance.

21 Claims, No Drawings

OTHER PUBLICATIONS cling", 3rd ed., vol. IX, Proteins and Peptides, pp. 135–136.

Payne, Donna W et al., "Enzymatic Estimation of Steroids in Subpicomole Quantities by Hydroxysteroid Dehydrogenases and Nicotinamide Nucleotide Cycling", *Jrn. of Biological Chemistry*, vol. 257, No. 2, Jan. 22, 1982, pp. 633–642.

Ratner, B. D. and Horbett, T. A., *Methods in Enzymology*, "Enzymatically Controlled Drug Release Systems". vol. 112, (1985), pp. 484–495.

Shier, W. Thomas, *Methods in Enzymology*, "Lectins as Carriers: Preparation and Purification of a Concanavatin A—Trypsin Conjugate", vol. 112 (Academic Press Inc., 1985), pp. 248–269.

Srere, Paul A., "Complexes of Sequential Metabolic Enzymes[1], [2]", *Ann. Rev. Biochem.*, vol. 56, 1987, pp. 89–124.

Voller, A., Diagnostic Horizons 2 Nol:1–6 (1978).

McDougal, J., et al., Jour Immunol Methods 76:171–183 (1985).

Kurstak, E., "Principles of the Design of Enzyme Immunoassays" in Enzyume Immunodiagnosis (Academic Press), pp. 23–54 (1986).

SIMULTANEOUS IMMUNOASSAY FOR THE DETERMINATION OF ANTIGENS AND ANTIBODIES

BACKGROUND OF THE INVENTION

Antigen-antibody reactions are part of the naturally occurring immune response of man and other animals upon exposure to foreign substances. Antibodies are derived from a class of proteins found in blood serum referred to as immunoglobulins. The presence of antigenic substance in the host organism results in the synthesis of immunoglobulin capable of binding to the antigen to form an antibody-antigen complex. The binding is characterized by a high degree of specificity and a high association constant between the antibody and antigen. The region of the antigen which participates in binding is called the epitope, and the region of the immunoglobulin participating in binding is called paratope. The high degree of specificity and affinity between antibodies and antigens has permitted the development of highly sensitive and specific methods of determining the presence and/or concentration of these substances. The methods are significant in the diagnosis of disease. Detection of antigens or antibodies to antigenic substances depends on the ability to distinguish between antibody-antigen complexes and the free forms of either antigen or antibody.

There are a number of prior art techniques for detection of antigens and antibodies. These methods include agglutination reactions with cells to form an insoluble particulate of latex or silica, gel diffusion, complement fixation, immunoelectrophoresis, Western blotting, fluorescent antibody techniques, radioimmunoassay, sandwich enzyme-linked immunoabsorbent assays and enzyme modulation immunoassays.

Immunochemical tests have important application for detecting the human immune deficiency virus (HIV) associated with the disease acquired immune deficiency syndrome (AIDS). The usefulness of determining the presence of the HIV in blood or blood products is evidenced by the resulting reduction in the number of persons contracting the disorder AIDS by receiving HIV in contaminated blood or blood products. Methods for the detection of antibodies to HIV and antigens produced by HIV have been described in the literature. (See, e.g., Groopman et al., Serological Characterization of HTLV-III Infection in AIDS and Related Disorders, "153 *J. of Infectious Diseases* 736 (1986); Allen, "A New HTLV-III/LAV Encoded Antigen Detected by Antibodies from AIDS Patients," 230 *Science* 810 (1985); Sarngadharan et al., "Antibodies Reactive with Human T-Lymphophilic Retrovirus (HTLV-III) in the Serum of Patients with AIDS," 224 *Science* 506 (1984); Gallo et al., "Frequent Detection and Isolation of Cyclopathic Retrovirus (HTLV-III) from Patients with AIDS and at Risk for AIDS," 224 *Science* 500 (1984).

One test currently employed for the detection of HIV is based on a technique called ELISA (enzyme-linked immunoabsorbent assay). According to this method, viral proteins from disrupted viral particles are coated on a plastic surface. The protein is exposed to a patient's serum and allowed to incubate. If the patient's serum contains antibodies to these proteins, they will bind to the viral proteins on the plastic surface. Unbound antibodies are removed by washing. Anti-human antibodies labelled with an enzyme (signal amplifier) are then incubated with the washed plastic surface. The enzyme-labelled antibodies will bind to any HIV antibodies retained on the HIV-coated plastic surface. Then a second wash is performed to remove any unbound anti-human antibodies. A substrate is added, which is converted by the enzyme label to a colored product indicating the presence of HIV antibodies in the sample. Although the method has good sensitivity and specificity, any positive specimen must be confirmed by Western blotting. This HIV test method requires expensive equipment, employs a time-consuming protocol and requires highly skilled personnel to perform the procedure. The technique is not easily performed by physicians in their offices, but requires the collection of a specimen for testing to be performed in a laboratory. Shipping of the specimen may lead to loss, damage or deterioration of the specimen prior to completion of the testing.

The presence of detectable antigen and antibodies to HIV during the course of the AIDS infection is not predictable with certainty and varies among patients. Generally, HIV antigen can be detected throughout the course of the infection, although there have been exceptional cases where neither antigen nor antibodies has appeared until 14 months after infection. IgM antibodies to HIV can usually be detected 2-3 weeks following exposure, and IgG antibodies appear detectably by the 12th week. Current FDA-approved AIDS tests detect only IgG antibodies, which means that there is a period during which infected blood may slip through screening procedures. Like ELISA, the present invention offers the advantage of being able to detect both IgM and IgG antibodies to HIV. In addition, IgA and IgE antibodies to HIV can also be detected. Thus, the period during which antibodies to HIV cannot be detected in blood specimens is considerably reduced by employing the immunoassay of the present invention.

Therefore, the object of the present invention is to provide an immunochemical assay for the determination of the presence or concentration of antigen or antibody in a fluid sample that is highly sensitive and specific, easily performed at low cost without the necessity of highly trained personnel or expensive laboratory equipment and which can be used, for example, for the detection of the AIDS virus.

SUMMARY OF THE INVENTION

The principal of operation of the immunochemical assays according to the present invention is the production of a detectable signal when two differently labelled antibodies are bound to the same antigen, or two differently labelled antigens are bound to the same antibody. This technique can be employed for determining the presence or amount of either antigen or antibody in very small concentrations.

The assays according to the invention are collectively referred to as Simultaneous ImmunoAssay, abbreviated SIA. The invention may be described with reference to the following diagram:

| substrate | signal | substrate | signal |
|---|---|---|---|
| $L_1$ | $L_2$ | $L_1$ | $L_2$ |
| Ag | Ag | Ab | Ab . |
| | Ab | | Ag | where
Ab symbolizes antibody;

Ag symbolizes antigen;
Ab-$L_1$ symbolizes antibody conjugated to label 1;
Ab-$L_2$ symbolizes antibody conjugated to label 2;
Ag-$L_1$ symbolizes antigen conjugated to label 1; and
Ag-$L_2$ symbolizes antigen conjugated to label 2.

The immunochemical assay may be used for detecting the presence or concentration of an antigenic substance in a fluid, by (1) forming a ternary complex of an antibody or antibody fragment conjugated to a first label (Ab-$L_1$), a second antibody or antibody fragment conjugated to a second label (Ab-$L_2$), and the antigenic substance in the fluid (Ag); and (2) detecting a signal produced in the presence of at least one substrate by the interaction of the first and second labels, enhanced by their proximity to each other bound to the antigenic substance. The immunochemical assay may be used for detecting the presence or concentration of an antibody in a fluid, by (1) forming a ternary complex of an antigenic substance conjugated to a first label (Ag-$L_1$), a second antigenic substance conjugated to a second label (Ag-$L_2$), and the antibody in the fluid (Ab); and (2) detecting a signal produced in the presence of at least one substrate by the interaction of the first and second labels, enhanced by their proximity to each other bound to the antibody.

The immunochemical assay may also be used in a competition reaction mode for detecting the presence or concentration of an antigenic substance in a fluid, by (1) forming, in the presence of the antigenic substance to be determined, a ternary complex of the antigenic substance conjugated to a first label, the antigenic substance conjugated to a second label, and an antibody to the antigenic substance; and (2) detecting a signal produced in the presence of at least one substrate by the interaction between said first label and said second label enhanced by their proximity to each other bound to the antibody. The immunochemical assay may also be used in a competition reaction mode for detecting the presence or concentration of an antibody in a fluid, by (1) forming, in the presence of the antibody to be determined, a ternary complex of the antibody conjugated to a first label, the antibody conjugated to a second label, and an antigenic substance; and (2) detecting a signal produced in the presence of at least one substrate by the interaction between said first label and said second label enhanced by their proximity to each other bound to the antigenic substance.

DETAILED DESCRIPTION OF THE INVENTION

In the non-competitive immunochemical assay for an antigenic substance, antibody conjugated with the first label (Ab-$L_1$) binds to antigen, and antibody conjugated with the second label (Ag-$L_2$) binds to the same antigen to form a ternary antigen-antibody complex. The interaction between the first label and the second label produces a detectable signal. This signal is generated by the action of the first label on a first substrate, followed by the action of the second label on a second substrate, which was produced in the first reaction. The interaction of the first and second labels conjugated to unbound antibodies in free solution is such that the detectable signal caused by such interaction is minimal; any substrate produced by the unbound first label may be scavenged from solution to prevent its reaction with the second label. The production of the signal is dependent upon the labels acting in concert, which is greatly enhanced by the presence of antigen, which brings the antibody-conjugated labels in proximity to each other when the ternary complex forms. The intensity of the signal generated is directly proportional to the amount of antigen present in the specimen. The non-competitive immunochemical assay for antibody functions in a similar manner, except that the signal is produced when antigen conjugated to a first label and antigen conjugated to a different second label bind to the same antibody.

The competitive immunochemical assays according to the present invention operate on the same principle (proximity of bound labels) as the non-competitive assays, except that the labels are conjugated to the substance that is to be determined in the sample. Accordingly, if there is antigen or antibody present, it competes with labelled antigen or antibody for binding sites, and the signal is less because the number of pairs of labels bound in proximity to each other is decreased in proportion to the amount of antigen or antibody present in the sample.

In one embodiment of the immunochemical assay according to the present invention, at least one of the labels is an enzyme that catalyzes a reaction of a substrate, the progress of which can be measured to give the signal. In a preferred embodiment of the invention, the first and second labels are each enzymes that catalyze sequential reactions, the progress of at least one of which can be measured to give a signal. In this preferred embodiment, the signal may be detected in a variety of ways. First, the appearance of the product of the second enzyme label acting on the second substrate may be measured. Second, the disappearance of the first substrate caused by the sequential action of the first and second enzyme labels may be measured. Third, if the enzyme labels are chosen such that the second label regenerates the first substrate, then the overall rate of the sequential reactions may be measured, constituting the signal. The progress of the enzyme reactions may be measured by endpoint detection after the reaction has been quenched, or preferably by a kinetic method in which the accumulation of reaction products is measured over time. The appearance or disappearance of enzyme reaction products may be measured directly, or in the alternative, the product or progress of subsequent reactions of these products, may be measured.

Possible pairs of enzyme labels for conjugation to antigen or antibody in the immunochemical assays according to the invention include glucose oxidase and horseradish peroxidase; horseradish peroxidase and luminol; and phosphoenol pyruvate kinase and luciferase.

Glucose oxidase catalyzes the reaction between glucose and molecular oxygen, producing hydrogen peroxide. Peroxidase catalyzes the oxidation of a variety of chromogenic substrates in the presence of hydrogen peroxide. The activity of glucose oxidase provides hydrogen peroxide as a substrate for the peroxidase-catalyzed oxidation of substrate, such as ortho-phenylenediamine. The rate of the peroxidase-catalyzed oxidation is significantly greater for those reactions catalyzed by peroxidase conjugated to an antigen bound to an antibody which also binds the glucose oxidaseconjugated antigen. The proximity of glucose oxidase and peroxidase in the antibody-(enzyme-labelled antigen) complex enhances the rate of the sequential catalytic reactions over that which occurs in free solution because hydrogen peroxide is made readily available to peroxidase. The extent of the peroxidase-catalyzed oxidation can be measured by observing a color change in the chromogenic substrate. The presence of a scavenger for hydrogen peroxide, such as catalase, decreases the background caused by the action of peroxidase conjugated to unbound antigen or antibody on hydrogen peroxide in free solution.

Peroxidase breaks down hydrogen peroxide to oxygen and water. Luminol produces light in the presence of oxygen. Therefore, peroxidase and luminol can be paired as enzyme labels. Upon addition of hydrogen peroxide to a sample containing antibodies or antigen, light is produced, the intensity of which can be measured with a photodiode. When peroxidase-labelled antigen and luminol-labelled antigen are bound to the same antibody, the intensity of emitted light increases because oxygen is made readily available to luminol.

Phosphophenol pyruvate kinase ($E_1$) and luciferase ($E_2$) catalyze the following coupled reactions:

$$\text{phosphophenol pyruvate} + \text{ADP} \xrightarrow{E_1} \text{pyruvate} + \text{ATP}$$

$$\text{luciferin} + \text{ATP} + O_2 \xrightarrow{E_2} \text{light} + CO_2 + \text{AMP} + \text{oxyluciferin}$$

The light produced by the luciferase-catalyzed reaction is greatly enhanced by the proximity of the pyruvate kinase and luciferase conjugates bound to the same antibody or antigen. The light may be measured with a scintillation counter.

In addition to enzyme conjugates, other types of labels may be used in the immunochemical assays of the present invention. For example, luminol and fluorescein may be paired as labels, in which case there is a chemiluminescent signal. When luminol-labelled antibody or antigen binds in proximity to fluorescein-labelled antibody or antigen, there is shift in the wavelength of light emitted, which can be measured with a luminometer.

Suitable antigen for conjugation with label must be of maximum purity and specificity. Inactivated antigen may be used, and it may be oxidized with chloramine T or periodate before conjugation. Unconjugated label and antigen can be separated from the labelled antigen by gel filtration chromatography or dialysis, depending on the molecular weight of the label. The label must also be of maximum purity; if enzymes are employed as labels, they must be of the maximum purity and specificity reasonably obtainable. The conjugation of antibody or antigen with label is made using techniques known in the prior art. In the case of enzyme conjugates, see *Methods in Enzymology*, Vol. 37, p. 133 (1975). In the case of fluorescent conjugates, see N.B. Cherry et al., *Staining Technologies* 44, 179 (1962).

Suitable antibodies for conjugation with label are capable of reaction with the same antigen and be affinity purified. The antibodies may be monoclonal antibodies specific for different epitopes on the same antigenic substance. The antibodies may also be Fab or $Fab_2$ antibody fragments produced by the digestion of the antibody with papain or pepsin, respectively.

The immunochemical assays according to the invention may be employed for both qualitative and quantitative determination of antibody or antigen because the strength of the signal produced is proportional to the amount of antigen or antibody present in the sample of fluid. Concentration may be determined by comparing the signal measured for the sample of antigen or antibody to the signals produced by a series of known concentrations of the antigen or antibody.

The present invention can be more thoroughly understood with reference to the following non-limiting examples.

EXAMPLE I

Reaction of Enzyme-Labelled HIV With HIV Antibodies

HIV antigen prepared from H-9 lysate and inactivated at a concentration of 1 mg/ml (Cytotek) was reacted with chloramine-T (2 mg/ml) at 2°–4° C. for 2 hours on ice. The unreacted chloramine T was removed by centrifugation at 700 times gravity for 10 minutes using a Centricon 10 ® microconcentrator device (Amicon, mfr.). The retained portion containing the oxidized HIV antigen was washed twice with ice cold phosphate buffered saline (PBS) using the same device.

The oxidized HIV antigen was readjusted to original volume and reacted with 100 equivalents of biotin hydrazide based on a molecular weight of 40,000 for HIV antigen overnight (16 hours) at 2–4° C. Removal of unreacted biotin hydrazide and low molecular weight products was accomplished by centrifugal separation as described above. Biotinylation was determined by serial microtiter assays using avidin peroxidase conjugate at 1:6000 dilution incubated for 30 minutes with orthophenylene diamine substrate.

The biotinylated HIV antigen was divided into two equal quantities, and a molar equivalent amount of avidin-conjugated glucose oxidase was added to one half and a molar equivalent of avidin-conjugated horseradish peroxidase was added to the remaining half of the biotinylated HIV antigen. The solutions were allowed to equilibrate overnight at 2–4° C. Excess unlabelled avidin was added to block any available biotin remaining unbound to avidin. The final concentration of the labelled-antigen preparations was 1 ng/μl.

HIV positive specimens determined by an FDA-approved ELISA test procedure (ABBOTT) and confirmed by Western blotting, and a specimen determined to be negative by the ELISA test were tested using the reagents described above. Results were determined by simple color comparison using reagent blanks as controls.

A substrate solution was prepared using 100 mM glucose and orthophenylene diamine (1 mg/ml) in 50 mM citrate-phophate buffer (pH 5.3).

To determine the optimal volume and concentration for reactivity of the reagents, a weakly reactive specimen (1:10 by ABBOTT) and a strongly reactive specimen (1:5000 by ABBOTT) were diluted to 1/10 and 1/20 of the original concentration. Varying volumes of the diluted specimen were placed in microtiter plates, and 1 μl of each enzyme-labelled antigen preparation was added to each plate.

The serum dilutions were incubated with the labelled antigen preparations for 5 minutes at 37° C., followed by addition of 100 μl of the substrate solution and incubation at room temperatue (25° C.±2° C.) for 5 minutes. The two sets of blank microtiter plates were prepared with volumes of PBS (pH 7.4) equal to the volumes of the serial dilutions employed. To the first set of blank plates (row G), one microliter of each enzyme-antigen conjugate was added, incubated for 5 minutes at 37° C., followed by an addition of 100 μl of substrate solution and incubation for 5 minutes at room temperature (25°±2° C.). No enzyme-antigen conjugate solution was added to the second set of blank solutions (row H); instead they were merely incubated with 100 μl of substrate solution. Prior to substrate addition, 100 μl of .1% TWEEN 20 .1% crystalline bovine serum albumin 4% polyethylene glycol (M.W. 3500) in PBS (pH 7.4) was added to each specimen and blank plate. The reaction was stopped by addition of 50 μl of 2N $H_2SO_4$. The results are shown in Table I.

TABLE I

| Specimen Volume | | .5 μl 1 | 1.0 μl 2 | 1.5 μl 3 | 2.0 μl 4 | 3.0 μl 5 | 4.0 μl 6 | 5.0 μl 7 |
|---|---|---|---|---|---|---|---|---|
| SR (NEAT) | A | Neg. | Neg. | Pos. | Pos. | Pos. | Pos. | Pos. |
| WR (NEAT) | B | Neg. | Neg. | Neg. | Neg. | Pos. | Pos. | Pos. |
| SR 1/10 | C | Neg. | Neg. | Neg. | Neg. | Pos. | Pos. | Pos. |
| WR 1/10 | D | Neg. | Neg. | Neg. | Neg. | Neg. | Pos. | Pos. |
| SR 1/20 | E | Neg. | Neg. | Neg. | Neg. | Neg. | Neg. | Pos. |
| WR 1/20 | F | Neg. | Neg. | Neg. | Neg. | Neg. | Neg. | Neg. |
| Control 1 | | Neg. | Neg. | Neg. | Neg. | Neg. | Neg. | Neg. |
| Control 2 | | Neg. | Neg. | Neg. | Neg. | Neg. | Neg. | Neg. |

1 μl of each glucose oxidase- and peroxidase-labelled HIV antigen solution (1 ng/μl) was added to each plate. The reaction was stopped 5 minutes after substrate addition with 50 μl 2N $H_2SO_4$.
SR = strongly reactive by ELISA
WR = weakly reactive by ELISA
Neg. = amount of color change less than or equal to that observed for Control 1
Pos. = amount of color change greater than that observed for Control 1
Control 1 = PBS (pH 7.4) + enzyme-antigen conjugates + substrate solution
Control 2 = PBS (pH 7.4) + substrate solution
Note: The strongly reactive specimens showed a markedly greater color change than did the weakly reactive specimens.

The above-described procedure was repeated with a second set of microtiter plates. This time 0.25 units of beef liver catalase (65,000 units/mg based on $H_2O_2$ substrate Boeringer, Mannheim) was added to each plate before addition of the substrate solution in order to scavenge hydrogen peroxide from the solution. The color change observed for the blank solutions, representing background, was thereby reduced. The results are shown in Table II.

TABLE II

| Specimen Volume | | 0.5 μl 1 | 1.0 μl 2 | 1.5 μl 3 | 2.0 μl 4 | 3.0 μl 5 | 4.0 μl 6 | 5.0 μl 7 |
|---|---|---|---|---|---|---|---|---|
| SR (NEAT) | A | Neg. | Neg. | Pos. | Pos. | Pos. | Pos. | Pos. |
| WR (NEAT) | B | Neg. | Neg. | Neg. | Neg. | Pos. | Pos. | Pos. |
| NR (NEAT) | C | Neg. | Neg. | Neg. | Neg. | Neg. | Neg. | Neg. |
| SR 1/10 | D | Neg. | Neg. | Neg. | Neg. | Pos. | Pos. | Pos. |
| WR 1/10 | E | Neg. | Neg. | Neg. | Neg. | Neg. | Pos. | Pos. |
| NR 1/10 | F | Neg. | Neg. | Neg. | Neg. | Neg. | Neg. | Neg. |
| Control 1 | | Neg. | Neg. | Neg. | Neg. | Neg. | Neg. | Neg. |
| Control 2 | | Neg. | Neg. | Neg. | Neg. | Neg. | Neg. | Neg. |

1 μl of each glucose oxidase- and peroxidase-labelled HIV antigen solution (1ng/μg) were added to each plate. The reaction was stopped 5 minutes after substrate addition with 50 μl 2N $H_2SO_4$.

EXAMPLE II

Reaction of Enzyme-labelled Antibodies to HIV Antigen

Goat antibodies to HIV (polyclonal IgG) were enzymatically treated on immobilized papain to provide monovalent Fab fragments.

The Fab fragments were adjusted to a concentration of 1 ng/μl protein concentration and biotinylated using NHS-biotin for 1 hour at 25° C. with stirring. Unreacted NHS-biotin was removed using a Centricon-10 ® separation device at 700 times gravity for 10 minutes. The biotinylated antibody fragments were washed three times with PBS (pH 7.4). All reagents were azide free. The use of excess NHS-biotin was avoided to prevent inactivation of the antigen binding capacity of the Fab fragments. Biotin conjugation was determined by serial dilutions in a microtiter assay using avidin peroxidase at 1:6000 dilution incubated for 30 minutes with orthophenylenediamine substrate.

The Fab-biotin conjugate was brought to a concentration of 1 ng/μl. Half of this solution was reacted with an equimolar amount of avidin-glucose oxidase conjugate and the other half was reacted with avidin-peroxidase conjugate. Excess unconjugated avidin was added to each reaction mixture to block any unbound biotin. Calculations of equivalency were based on Fab M.W. of 80,000.

HIV antigen, disrupted and inactivated (Cytotek), was serially diluted with a solution of PBS (pH 7.4)+0.1% TWEEN 20+0.1% crystalline bovine serum albumin to obtain six dilutions ranging in concentration from 1 μg/ml to 10 pg/ml. 100 μl of each serial dilution was added to 40 microtiter plates. A 5 ng/ml solution of each of the enzymelabelled Fab fragments was diluted to obtain 0.5, 1, 2, 3, 4, and 5 ng/μl solutions. One μl of each of these antibody fragment solutions was added to each serial dilution of HIV antigen and incubated for 5 minutes at 27° C. Then 200 μl of orthophenylenediamine substrate was added to each plate and incubated for 5 minutes at 25°±2° C. The reaction was stopped by the addition of 50 μl of 2N $H_2SO_4$. In addition, 0.25 units of beef liver catalase (65,000 units/mg based on $H_2O_2$ substrate Boeringer, Mannheim) was added to each plate as a hydrogen peroxide scavenger. The results are recorded in Table III.

TABLE III

| [Ag]g/ml | $10^{-6}$ | $10^{-7}$ | $10^{-8}$ | $10^{-9}$ | $10^{-10}$ | $10^{-11}$ |
|---|---|---|---|---|---|---|
| [Ab-L] | 1 | 2 | 3 | 4 | 5 | 6 |
| 5 ng/μl | Neg. | Pos. | Pos. | Pos. | Pos. | Pos. |
| 4 ng/μl | Neg. | Pos. | Pos. | Pos. | Pos. | Pos. |
| 3 ng/μl | Neg. | Neg. | Pos. | Pos. | Pos. | Pos. |
| 2 ng/μl | Neg. | Neg. | Pos. | Pos. | Pos. | Neg. |

TABLE III-continued

| [Ag]g/ml | $10^{-6}$ | $10^{-7}$ | $10^{-8}$ | $10^{-9}$ | $10^{-10}$ | $10^{-11}$ |
|---|---|---|---|---|---|---|
| [Ab-L] | 1 | 2 | 3 | 4 | 5 | 6 |
| 1 ng/μl | Neg. | Neg. | Pos. | Pos. | Pos. | Neg. |
| 0.5 ng/μl | Neg. | Neg. | Neg. | Pos. | Neg. | Neg. |
| Control 1 | Neg. | Neg. | Neg. | Neg. | Neg. | Neg. |
| Control 2 | Neg. | Neg. | Neg. | Neg. | Neg. | Neg. |

EXAMPLE III

Determination of Thyroxine Concentration in Blood Serum

Thyroxine is a haplenizable molecule. The presence of thyroxine in serum samples was determined by using thyroxine-free serum spiked with known quantities of thyroxine over the range of 1–10 nmoles/ml. In this experiment, thyroxine in the serum samples competes with enzyme-labelled thyroxine added to the serum for binding sites on anti-thyroxine antibodies. The rate of the sequential reactions catalyzed by the two enzyme labels is directly related to the number of antibodies binding to each of the two enzyme-labelled antigens and therefore inversely related to the amount of unlabelled thyroxine in the serum samples.

Thyroxine was conjugated to phosphenol pyruvate kinase using SPDP (N-succinimidyl-3-(2-pyrrolyl-dithio) propionate). Bound and unbound materials were separated by gel filtration chromatography. Luciferase was conjugated to thyroxine using a similar procedure.

The substrate concentrations used for assay of the coupled reaction between pyruvate kinase and luciferase were those described in Bergmeyer, *Methods of Enzymatic Analysis,* Academic Press, New York (1974). The amount of light emitted in each reaction was measured using a scintillation counter with the coincidence device disconnected. Counts were taken for 30 seconds following the injection of the substrate solution and mixing.

The amount of thyroxine present in the serum samples was determined by incubating the serum with 7.5 nmole equivalents of pyruvate kinase-labelled thyroxine and 7.5 nmole equivalents of luciferase-labelled thyroxine for 20 minutes at room temperature in the presence of rabbit antibodies to thyroxine. Substrate was then added and the lightemitting reaction was read as described above. The thyroxine found in spiked samples was found to have an inverse relationship to the amount of light counted on the scintillation counter. When the results found by the above-described luminescent procedure compared to the results of the standard radioimmunoassay procedure, a correlation ratio of 96% was found between the values obtained.

EXAMPLE IV

Detection of Antibodies

Goat and rabbit antibodies (Sigma) were labelled with pyruvate kinase (Sigma: rabbit muscle) and with luciferase (LKB) in separate reactions using the SPDP method. The substrate solution employed in the assay was that described by Bergmeyer, supra. Normal rabbit, human, and mouse serum were obtained from Pel Freeze.

Scintillation vials were filled with 50 μl of serum, diluted with PBS (pH 7.4) to concentrations ranging from 1:100 to 1:1,000,000 (v/v). The goat and rabbit enzyme-antibody conjugates were diluted 1:5000, and 25 μl was added to each vial and equilibrated for 30 minutes at 37° C. with the caps tightly sealed. The substrate buffer solution was concentrated such that final concentrations in the reaction mixture would be optimal. 50 μl of the substrate solution was injected into each vial and mixed. Each vial was counted for 30 minutes in a scintillation counter.

Both the rabbit and goat serum dilutions ranging from 1:100 to 1:1000 produced significant reaction. Only the rabbit serum which was diluted more than 1:1000 gave a signal greater than the blank consisting of substrate and conjugate only. The optimum rabbit serum dilution was at 1:500,000 dilution.

The above-described examples illustrate, but do not limit the present invention. It will be appreciated by those skilled in the art that many variations in the above-described procedures and materials are possible within the scope of the appended claims.

What is claimed is:

1. An immunochemical assay to determine the presence or concentration of an antigenic substance in a fluid, comprising:
   (a) contacting with said fluid to form a complex with said antigenic substance if any said antigenic substance is present is said fluid:
      (1) a first aliquot of an antibody or antibody fragment conjugated to a first label and capable of binding with said antigenic substance, and
      (2) a second aliquot of the same antibody or antibody fragment conjugated to a second label;
      (3) said first or second label capable of reacting with a substrate to produce a reaction product which can interact with said other first or second label to generate a signal, and
   (b) detecting the presence or absence of a signal as a determination of the presence or concentration of said antigenic substance in said fluid.

2. An immunochemical assay to determine the presence or concentration of an antibody in a fluid, comprising:
   (a) contacting with said fluid to form a complex with said antibody if any said antibody is present in said fluid:
      (1) a first aliquot of an antigenic substance or hapten conjugated to a first label and capable of binding with said antibody, and
      (2) a second aliquot of the same antigenic substance or hapten conjugated to a second label;
      (3) said first or second label capable of reacting with a substrate to produce a reaction product which can interact with said other first or second label to generate a signal, and
   (b) detecting the presence or absence of a signal as a determination of the presence or concentration of said antibody in said fluid.

3. An immunochemical assay to determine the presence or concentration of an antigenic substance in a fluid comprising:
   (a) contacting with said fluid to form a complex with said antigenic substance if any said antigenic substance is present in said fluid:
      (1) first aliquot of a monoclonal antibody conjugated to a first label and capable of binding with an epitope on said antigenic substance,
      (2) a second aliquot of the same monoclonal antibody conjugated to a second label, and
      (3) said first or second label capable of reacting with a substrate to produce a reaction product which can interact with said other first or second label to generate a signal, and (b) detecting the presence or absence of a signal as a determination of the presence or concentration of said antigenic substance in said fluid.

4. An immunochemical assay to determine the presence or concentration of an antigenic substance in a fluid comprising:

(a) adding to said fluid to form a complex with said antigenic substance if any said antigenic substance is present in said fluid;
  (1) a first aliquot of an antibody fragment conjugated to a first label and capable of binding with an epitope on said antigenic substance, and
  (2) a second aliquot of the same antibody fragment conjugated to a second label,
  (3) said first or second label capable of reacting with a substrate to produce a reaction product which interacts with said other first or second label to enable said other first or second label to generate a signal, and (b) detecting the presence or absence of a signal as a determination of the presence or concentration of said antigenic substance in said fluid.

5. The immunochemical assay according to claim 4, wherein the antibody fragment is a monovalent fragment (Fab) produced by digestion of the antibody with papain.

6. The immunochemical assay according to claim 4, wherein the antibody fragment is a bivalent fragment (Fab$_2$) produced by digestion of the antibody with pepsin.

7. An immunochemical assay to determine the presence or concentration of an antigenic substance in a fluid, comprising:

(a) contacting with said fluid a first aliquot of the antigenic substance conjugated to a first label, a second aliquot of the antigenic substance conjugated to a second label, and an antibody to said antigenic substance; said first or second label capable of reacting with a substrate to produce a reaction product which can interact with said other first or second label to generate a signal, and (b) detecting the presence or absence of a signal as a determination of the presence or concentration said antibody in said fluid.

8. An immunoassay to determine the presence or concentration of antibody fluid, comprising:

(a) contacting with said fluid a first aliquot of the antibody conjugated to a first label, a second aliquot of the antibody conjugated to a second label, and an antigenic substance or hapten capable of binding with said antibody; said first or second label capable or reacting with a substrate to produce a reaction product which can interact with said other first or second label to generate a signal, and (b) detecting the presence or absence of a signal as a determination of the presence or concentration of said antigenic substance in said fluid.

9. The immunochemical assay according to claim 1, 2, 7 or 8, wherein said first label and said second label are each enzymes, and said signal is produced by the sequential action of said first enzyme label on or in the presence of a first substrate, and said second enzyme label on or in the presence of a second substrate, said second substrate being a product of the action of said first enzyme label on said first substrate.

10. The immunological assay according to claim 9, wherein said signal is an increased rate of appearance of said second substrate.

11. The immunological assay according to claim 9, wherein said signal is an increased rate of disappearance of said first substrate.

12. The immunological assay according to claim 9, wherein said signal is an increased rate of a set of cyclic reactions, in which said first substrate is regenerated by the action of said second enzyme label on or in the presence of said second substrate.

13. The immunochemical assay according to claim 10, wherein the first enzyme label is glucose oxidase, the second enzyme label is horseradish peroxidase, the first substrate is glucose, the second substrate is hydrogen peroxide, and the signal is a color change in the presence of orthophenylenediamine.

14. The immunochemical assay according to claim 10, wherein the first enzyme label is horseradish peroxidase, the second label is not an enzyme but luminol, the first substrate is hydrogen peroxide, the second substrate is oxygen, and the signal is light.

15. The immunochemical assay according to claim 10, wherein the first enzyme label is phosphenol pyruvate kinase, the second enzyme label is luciferase, the first substrate is phosphenol pyruvate, and the signal is light.

16. A process for determining the presence or concentration of antibody to an antigenic substrate or hapten in a fluid, comprising the steps of:

(a) contacting the fluid with a solution of the antigenic substance or hapten said solution containing a first aliquot of the antigenic substance or hapten conjugated to a first enzyme label and a second aliquot of the same antigenic or hapten conjugated to a second enzyme label, in order to form a complex of said antibody in said fluid if any of said antibody is present in said fluid said first enzyme-labelled antigen or hapten and said second enzyme-labelled antigen or hapten; said first enzyme capable of reacting with a substrate to produce a reaction product which can interact with said other second label to generate a signal;

(b) contacting the complex solution with a substrate for said first enzyme label, in order to form a reaction product of said first enzyme label and said substrate;

(c) measuring a signal produced by the reaction of said second enzyme label in the presence of the reaction product formed in step (b);

(d)
  (i) relating the signal measured in step (c) to the signal measured for a control sample prepared according to steps (a) - (c), said control sample being free of antibody to said antigenic substance or hapten in order to determine the presence of antibodies in said fluid sample; or
  (ii) relating the signal measured in step (c) to the signal measured for samples containing known amounts of the antibody prepared according to steps (a) - (c), in order to determine the concentration of said antibodies in said fluid.

17. A process for determining the presence or concentration of an antigenic substance in a fluid, comprising the steps of:

(a) contacting the fluid with a solution of antibodies to the antigenic substance, said solution containing a first aliquot of antibodies conjugated to a first enzyme label and a second aliquot of the same antibodies conjugated to a second enzyme label, in order to form a complex of an antigenic substance in the fluid, if any antigenic substance is present in the fluid, said first enzyme-labelled antibody and said second enzyme-labelled antibody; said first enzyme capable of reacting with a substrate to produce a reaction product which can interact with said second enzyme to generate a signal;

(b) contacting the complex solution with a substrate for said first enzyme label, in order to form a reaction product of said first enzyme label and said substrate.

(c) measuring a signal produced by the reaction of said second enzyme label in the presence of the reaction product formed in step (b);

(d)
  (i) relating the signal measured in step (c) to the signal measured for a control sample prepared according to steps (a)–(c), said control sample being free of said antigenic substance, in order to determine the presence of said antigenic substance in said fluid; or
  (ii) relating the signal measured in step (c) to the signal measured for samples containing known amounts of said antigenic substance prepared according to steps (a)–(c), in order to determine the concentration of the antigenic substance in said fluid.

18. The process according to claim 16, wherein the antibodies in the fluid are antibodies to the human immune deficiency virus.

19. The process according to claim 17, wherein the antigen in the fluid is human immune deficiency virus.

20. A process for determining the presence or concentration of an antigenic substance in a fluid, comprising the steps of:

(a) contacting the fluid with a solution containing the antigenic substance, said solution containing a first aliquot of the antigenic substance conjugated to a first enzyme label, a second aliquot of the same antigenic substance conjugated to a second enzyme label, and antibodies to said antigenic substance, in order to form a complex in which the antigenic substance in the sample competes with said enzyme labelled antigenic substances for binding sites on the antibody; said first enzyme capable of reacting with a substrate to produce a reaction product which can interact with said second enzyme to generate a signal;

(b) contacting the complex solution with a substrate for said first enzyme label, in order to form a reaction product of said first enzyme label and said first substrate;

(c) measuring a signal produced by the reaction of said second enzyme label in the presence of the reaction product formed in step (b);

(d)
  (i) relating the signal measured in step (c) to the signal measured for a control sample prepared according to steps (a)–(c), said control sample being free of said antigenic substance, in order to determine the presence of the antigenic substance in said fluid; or
  (ii) relating the signal measured in step (c) to the signal measured for samples containing known amounts of said antigenic substance prepared according to steps (a)–(c), in order to determine the concentration of the antigenic substance in said fluid.

21. A process according to claim 20, wherein the antigenic substance in the fluid is thyroxine.

* * * * *